(12) United States Patent
Huxel et al.

(10) Patent No.: US 6,503,259 B2
(45) Date of Patent: Jan. 7, 2003

(54) EXPANDABLE ANASTOMOTIC DEVICE

(75) Inventors: Shawn T. Huxel, Lawrenceville, NJ (US); John McAllen, III, Point Pleasant, NJ (US); David W. Overaker, Annandale, NJ (US)

(73) Assignee: Ethicon, Inc., Somerville, NJ (US)

( * ) Notice: Subject to any disclaimer, the term of this patent is extended or adjusted under 35 U.S.C. 154(b) by 13 days.

(21) Appl. No.: 09/748,311

(22) Filed: Dec. 27, 2000

(65) Prior Publication Data

US 2002/0082625 A1 Jun. 27, 2002

(51) Int. Cl.$^7$ ............................................. A61B 17/08
(52) U.S. Cl. .................. 606/153; 606/154; 606/220; 227/179.1; 227/181.1; 227/902; 411/337; 411/450; 411/923
(58) Field of Search ................... 606/153, 154, 606/220; 227/179.1, 181.1, 902; 411/450, 337, 923

(56) References Cited

U.S. PATENT DOCUMENTS

| | | | |
|---|---|---|---|
| 4,467,804 A | | 8/1984 | Hardy et al. |
| 4,476,863 A | * | 10/1984 | Kanshin et al. ............... 227/19 |
| 4,505,414 A | | 3/1985 | Filipi |
| 4,532,926 A | * | 8/1985 | O'Holla ..................... 606/220 |
| 4,552,148 A | | 11/1985 | Hardy, Jr. et al. |
| 4,573,469 A | * | 3/1986 | Golden et al. ............... 411/363 |
| 4,603,693 A | * | 8/1986 | Conta et al. ............. 227/179.1 |
| 4,766,898 A | | 8/1988 | Hardy et al. |
| 4,889,119 A | * | 12/1989 | Jamiolkowski et al. ...... 525/415 |
| 4,917,114 A | * | 4/1990 | Green et al. ............. 227/179.1 |
| 5,116,349 A | * | 5/1992 | Aranyi .................... 227/181.1 |
| 5,250,058 A | | 10/1993 | Miller et al. |
| 5,336,233 A | * | 8/1994 | Chen .......................... 606/153 |
| 5,346,501 A | * | 9/1994 | Regula et al. ............... 606/151 |
| 5,352,238 A | * | 10/1994 | Green et al. ............. 227/176.1 |
| 5,358,510 A | * | 10/1994 | Luscombe et al. .......... 606/151 |
| 5,423,858 A | * | 6/1995 | Bolanos et al. ................ 24/297 |
| 5,425,738 A | | 6/1995 | Gustafson et al. |
| 5,456,714 A | | 10/1995 | Owen |
| 5,464,450 A | * | 11/1995 | Buscemi et al. ............ 606/154 |
| 5,533,661 A | * | 7/1996 | Main et al. ............... 227/176.1 |
| 5,591,206 A | * | 1/1997 | Moufarrege ................. 606/153 |
| 5,632,433 A | * | 5/1997 | Grant et al. .............. 227/176.1 |
| 5,707,380 A | * | 1/1998 | Hinchliffe et al. .......... 606/153 |
| 5,997,573 A | * | 12/1999 | Quijano et al. ............. 606/153 |
| 6,036,704 A | | 3/2000 | Yoon |
| 6,050,472 A | * | 4/2000 | Shibata .................... 227/175.2 |
| 6,083,241 A | * | 7/2000 | Longo et al. ............. 227/179.1 |

FOREIGN PATENT DOCUMENTS

EP 147920 * 7/1985

* cited by examiner

Primary Examiner—Rodney M. Lindsey

(57) ABSTRACT

A surgical fastening system includes a fastener having a plurality of individual fastener pairs each having a piercing element with a pin that pierces the tissue to be repaired and a receiver portion that interlocks with the pin of a corresponding piercing element. A fastener dispenser holds the piercing elements and receiver elements in relative juxtaposition and in a predetermined geometric configuration, such as a circle. After the tissues to be joined are positioned between the piercing and receiving elements held in the dispenser, the dispenser is adjusted to draw the elements together capturing the tissue therebetween. The dispenser then pushes the piercing elements through the tissue and into the receiving elements causing the elements to interlock. Because the anastomosed junction is formed by a plurality of independent pairs, the junction retains flexibility. When used to anastomose a tubular organ, the fastener allows radial expansion of the organ permitting peristalsis.

21 Claims, 5 Drawing Sheets

EXPANDABLE ANASTOMOTIC DEVICE

FIELD OF THE INVENTION

The present invention relates to an apparatus and method for performing anastomosis, more particularly, using a plurality of interlocking fasteners that compress the anastomosed tissues together.

BACKGROUND OF THE INVENTION

After surgical resection of a diseased or cancerous portion of a tubular organ, e.g., partial bowel resection, the severed ends of the organ must be reconnected, or anastomosed. In this type of operation there are certain common objectives, viz., (i) to restore the integrity of the organ, i.e., so that no leakage through the repair occurs (ii) hemostasis of severed blood vessels while preserving blood flow to healthy tissue proximate the wound (iii) avoidance of further tissue damage by the anastomosis procedure (iv) preservation of organ function e.g., by avoiding the obstruction of the lumen of the organ or restraining peristalsis, if applicable. Present medical techniques for connecting two sections of a hollow tubular organ include suturing, stapling or clamping the severed ends together, each method having strengths and weaknesses relative to meeting the foregoing objectives.

For example, suturing is not preferred in certain circumstances due to the inaccessibility of one or both of the ends to be joined and/or the time and high degree of mechanical skill involved for performing the anastomosis. Staplers may be used to reconnect a severed tubular organ with a circular ring of staples distributed around a circumference to connect the severed ends. The resulting connection is radially compliant, allowing peristalsis in the region of the anastomosis, however, care must be taken to avoid over compression or incomplete apposition of the tissue. Since combined tissue thickness can vary by as much as 2 millimeters from patient to patient, the surgeon must adjust the stapler and resultant crimp length of the staples to accommodate the thicknesses that may be encountered. Further, the metallic staples are not absorbable.

The permanence of metallic anastomotic staples has been addressed by biodegradable anastomotic fastening systems which break down in the presence of bodily fluids at a predetermined rate. For example, U.S. Pat. No. 5,250,058 describes a biodegradable anastomotic fastener having a pair of plates, one of which has holes for receiving latching prongs protruding from the other plate. The plates are held in spaced relation on head and anvil sections, respectively, of an instrument that is inserted into the lumen of the organ to be repaired. The apposed ends of the organ are positioned between the fastener plates which are then drawn together by actuating the instrument. Fastening is accomplished through a singular linear motion in which the prongs of the first plate pierce the tissue then latch within the holes in the opposing plate. The excess tissue within the lumen is then cut by a cylindrical knife. The inner portion of each plate is also cut by the cylindrical knife to allow the instrument to be removed from the lumen of the organ. Known mechanized anastomosis fastening systems generally require tissue thickness to be measured to select an appropriate fastener and to avoid over compression or incomplete apposition. Accordingly, a variety of fastener sizes must be available to accommodate varying tissue thicknesses. In addition, known ring-type fastener systems provide a rigid anastomosis, limiting the radial expansion of the anastomosis and interrupting peristalsis.

SUMMARY OF THE INVENTION

The limitations of prior art surgical apparatus and methods for performing anastomosis are addressed by the present invention which includes a surgical fastener with a plurality of first portions having a first tissue constraining surface and a plurality of second portions having a second tissue constraining surface. The first portions are positionable proximate a first side of a bodily tissue, with the second portions positionable proximate a second side of the bodily tissue adjacent corresponding ones of the first portions. The first portions are extendable through the bodily tissue to contact the second portions and interlock therewith with the first tissue constraining surface positioned proximate the first side of the bodily tissue and resisting withdrawal of the first portions through the bodily tissue. The second tissue constraining surface is positioned proximate the second side of the bodily tissue resisting withdrawal of the second portion through the bodily tissue.

The fastener may be applied with a dispenser apparatus executing a method in accordance with the present invention, viz., the dispenser holds a plurality of individual fastener pairs, each having a first portion and a second portion, with the first portions on one side of the bodily tissue and the second portions on the other side. The dispenser ejects the first portions through the bodily tissue to contact the second portions and interlock therewith.

BRIEF DESCRIPTION OF THE DRAWINGS

For a better understanding of the present invention, reference is made to the following detailed description of various exemplary embodiments considered in conjunction with the accompanying drawings, in which.

DETAILED DESCRIPTION OF THE EXEMPLARY EMBODIMENTS

Figure 1:
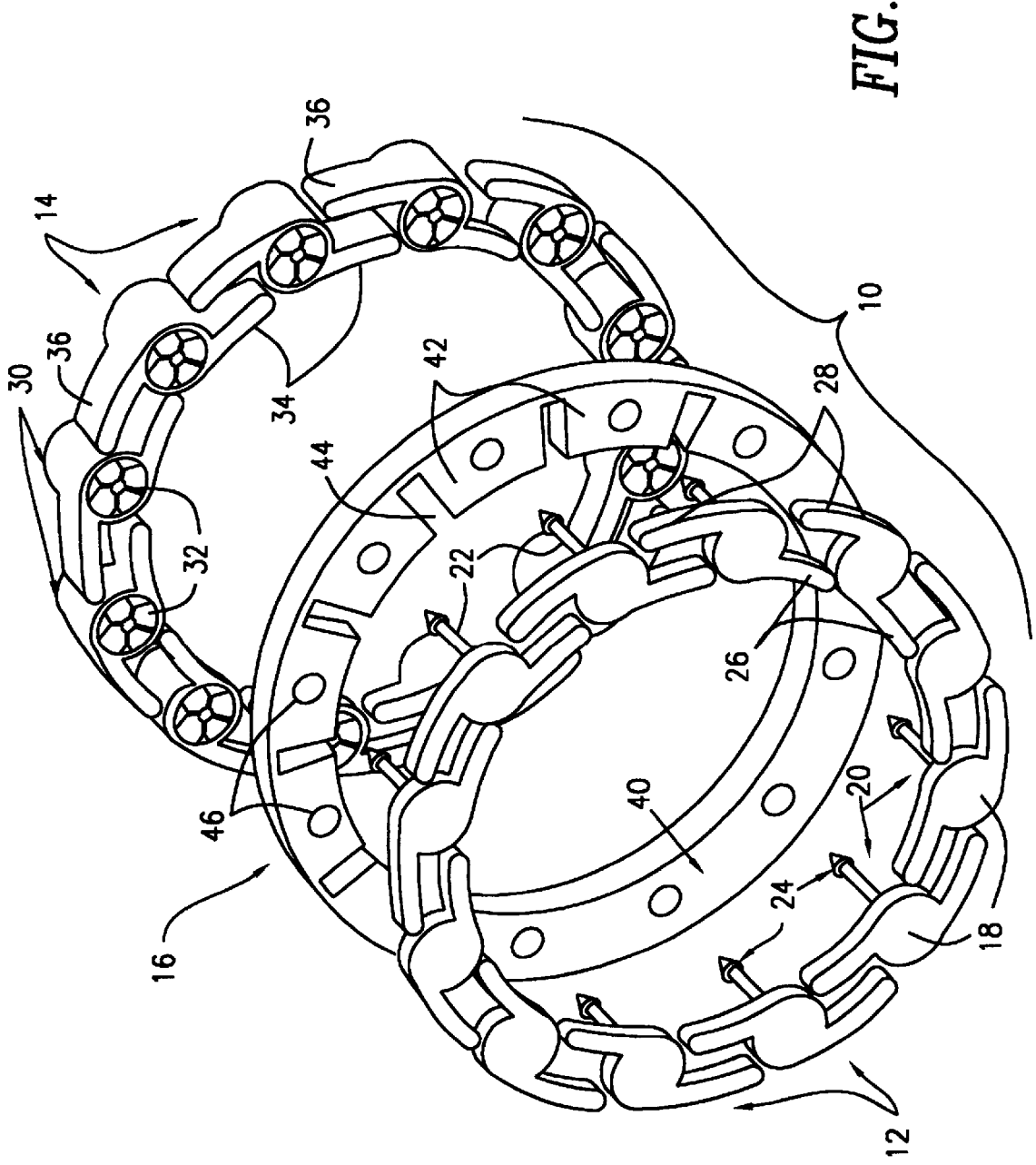
FIG. 1 is an exploded perspective view of a multi-part anastomotic fastener in accordance with the present invention.

FIG. 1 shows a fastener array 10 having a plurality of fasteners 11 (see FIG. 3), each having a tissue piercing element 12 and a receiver element 14. A gasket 16 may be interposed between the elements 12, 14 of the array 10. The piercing elements 12 have a base 18 from which a pin 20 extends perpendicularly. Each pin 20 has a shaft 22 and latching head 24. A pair of arms 26 (inner), 28 (outer) extend in opposite directions and generally tangentially from each base 18. (If the piercing elements 12 are rotated 180°, their inner and outer orientations are reversed, a configuration contemplated by the present invention). Each of the receiver elements 14 has a central portion 30 with an opening 32 for receiving a pin 20. A pair of arms 34 (inner), 36 (outer), preferably homologous (mirror images) relative to the arms 26, 28 of the piercing elements 12, extend from the central portion 30 of each receiver element 14, such that the arms 26, 28 and 34, 36 of juxtaposed piercing elements 12 and receiver elements 14 are opposed and compress the tissues to be joined therebetween when the fastener array 10 is applied. As shall be described further below, the multiple piercing elements 12 and receiver elements 14 of the fastener array 10 are held in relative alignment by a fastener dispenser 38 (See FIG. 4) prior to their use in anastomosis.

As shown in FIG. 1, the multiple elements 12, 14 may be held in a generally cylindrical configuration for the purpose of anastomosing a generally cylindrical organ such as the intestine. Other configurations, such as oval, rhomboid, octagonal, crescent, straight line, etc. could likewise be employed, depending upon the requirements of the surgical repair being made. For a given overall configuration, e.g., circular/cylindrical as shown in FIG. 1, the shape and spacing of the multiple elements 12, 14 impact the overall function of the fastener array 10. More particularly, FIG.1 shows that each fastener 11 in the fastener array 10 is positioned close to two adjacent fasteners 11 with the inner arm 26 of piercing element 12 extending towards and nearly touching base 18 of an adjacent piercing element 12 in the clockwise direction. Outer arm 28 extends in a direction opposite the inner arm 26 and nearly touching base 18 of the adjacent piercing element 12 in a counter-clockwise direction. Inner arm 26 and outer arm 28 of piercing element 12 extend from the base 18 along different radii, such that when the elements 12 are arranged in a generally circular configuration as shown in FIG. 1, the inner arms 26 and outer arms 28 approximate concentric segmented rings. Inner arm 34 and outer arm 36, respectively, of receiving element 14 extend from central portion 30 along the same radii as inner arm 26 and outer arm 28, respectively, of piercing element 12. The arrangement of receiver elements 14 approximates two concentric segmented rings and inner arm 26 and outer arm 28, respectively, of piercing element 12 are adjacent to inner arm 34 and outer arm 36, respectively, of receiving element 14 in fastener 11. When each fastener 11 is assembled, tissue residing between piercing element 12 and receiver element 14 in fastener 11 is subjected to compressive pressure through two concentric rings of contact, along with the contact provided by the base portions 18 acting against the central portions 30 of the receiver elements 14. This approximately continuous, evenly distributed and redundant compressive contact insures hemostasis and is provided by a plurality of independent fasteners 11 which can move relative to one another to allow expansion of the circular/cylindrical configuration of the fastener array 10 when it is applied to repair a flexible tubular organ such as the intestine. More specifically, each of the fasteners 11 is structurally independent. When the fastener array 10 is applied, each of the piercing elements 12 insert into and lockingly engage a corresponding retainer element 14 as further described below. It is preferred that once the elements 12, 14 interlock, that the elements 12, 14 of each interlocking pair forming each fastener 11 do not disassociate from each other. Each interlocked pair 12, 14 is structurally independent from any other pair of interlocked elements 12, 14, allowing the interlocked pairs of elements 12, 14 to move independently of the others, being constrained and held in relative proximity by their affixation to a common substrate, e.g., peripheral flanges of tissue on the conjoined severed ends of the intestine. This relative structural independence of the fasteners 11 gives rise to what can be described as "flexibility" of the fastener array 10. The flexibility of the fastener array 10 permits the organ to which it is applied to change its shape and dimensions, e.g., during the radial expansion and contraction associated with peristalsis.

A soft, flexible gasket 16 depicted in FIG. 1 functions to distribute the compressive forces exerted by the opposed elements 12, 14 on the anastomosed tissue to avoid over compression and to compensate for differences in tissue thickness. As shown in FIG. 1, the gasket 16 has a continuous portion 40 and a portion with a plurality of segments 42 defined by slots 44. The purpose of illustrating the gasket 16 in this manner is to show that the flexibility of the gasket 16 can be altered mechanically by providing discontinuities, e.g., slots 44, in addition to varying the material of composition. More particularly, the gasket 16 material can be chosen to be sufficiently flexible to allow the required radial expansion using a continuous gasket and/or the gasket 16 may be partially or completely segmented by slots 44 that pass through a portion or the entirety of the gasket 16. In the case of slots 44 that pass through the entirety of the gasket 16, a plurality of independent segments 42 are produced. A plurality of holes 46 in the gasket 16 permit the gasket 16 to be threaded over the plurality of pins 20 extending from the piercing elements 12. When the gasket 16 has slots 44 dividing it into a plurality of individual segments 42, a hole or holes 46 in each segment 42 retain the segment 42 in position relative to the fastener 10. The gasket 16 is optional in that the fastener 10 will function without it if the length of the pins 20 are properly matched to the thickness of the tissues anastomosed. While a single, generally circular gasket 16 is shown in FIG. 1, more than one gasket 16 can be employed, e.g., between the anastomosed tissue and elements 12 and between the tissue and element 14. The gasket 16 need not be circular or have dimensions approximating those of the fastener array 10, e.g., the gasket 16, may be octagonal, square or another shape and/or have dimensions larger than the fastener 10. The gasket 16 need not have a preformed central opening since the central opening may be made by the dispenser 38 cutter 82 as described below. Similarly, holes 46 are not required since the pins 20 of the piercing elements 12 can pierce the gasket 16 in the same way they pierce the anastomosed tissue.

Besides functioning as a force distributor and force moderator, the gasket 16 aids in maintaining hemostasis and apposition in the eventuality that one of the piercing elements 12 fails to engage with a mating receiver element 14. More particularly, the gasket 16 will bridge the space left by the missing interlocking pair of elements 12, 14, exerting compressive force against the anastomosed tissue, curtailing bleeding and maintaining the integrity of the junction. This same purpose is served by the alternating directions of the arms 26, 28 and 34, 36. More specifically, because the arms, e.g., 26, 28 extend in opposite directions from the base 18, if one element 12 is removed from the fastener array 10 depicted in FIG. 1, then the width of the resulting gap between elements 12 approximates the diameter of the base 18. The same can be said of the retainer elements 14. As the ring configuration of the fasteners 11 is expanded due to the expansion of the substrate to which it is applied, e.g., due to expansion of the radius of the bowel during peristalsis, the distance between the concentric ring contact areas, i.e., the distance between the inner arms 26, 34 and outer arms 28, 36 of the piercing elements 12 and receiving elements 14, respectively, of adjacent fasteners 11 is decreased and the gap between arms 26, 28 and the bases 18 (and between arms 34, 36 and central portions 30) is increased. Because there is a substantial degree of radial overlap of the inner and outer arms 26, 28 of adjacent elements 12 (and arms 34, 36 of adjacent elements 14), the fastener 10 continues to exhibit approximate concentric radial contact over a large range of expansion of the substrate to which the fastener 10 is affixed.

Figure 2:
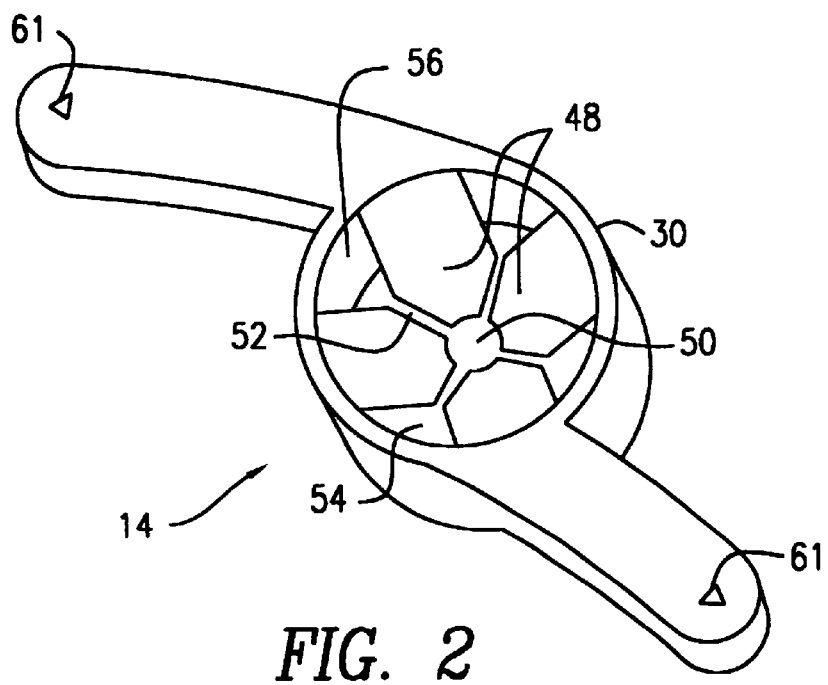
FIG. 2 is an enlarged perspective view of a receiver element of the device of FIG. 1.
Figure 3:
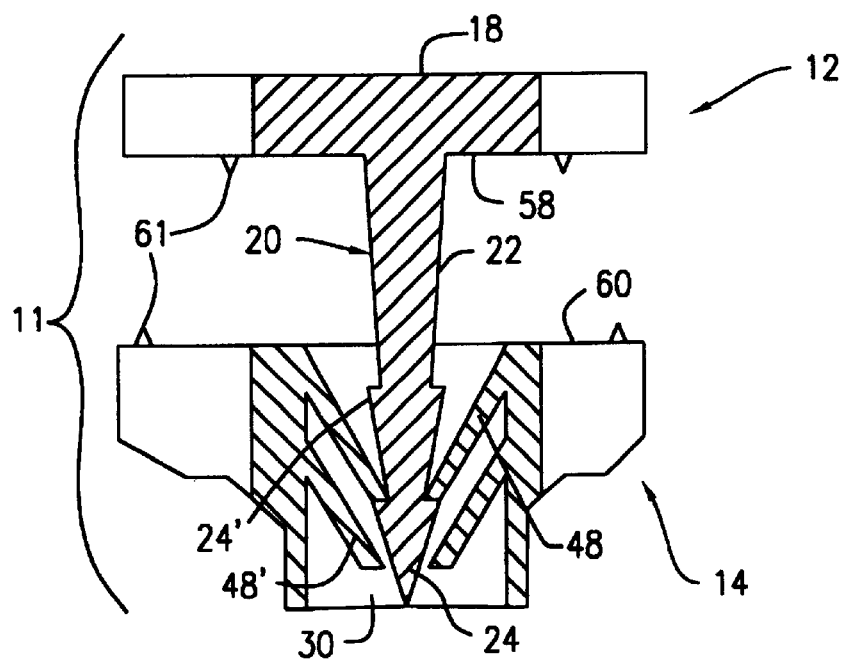
FIG. 3 is a cross-sectional side view of an individual piercing element and a corresponding receiver element of the device of FIGS. 1 and 2 in the engaged position.

FIGS. 2 and 3 show that each retainer element 14 has a plurality of flexible latch members 48 ramping inwardly towards the center of the central portion 30 and terminating at a free end thereof in a pin receiver opening 50 having dimensions approximating the outer diameter of the shafts 22 of the pins 20, the pin receiver opening 50 being defined by the relative spacing between the plurality of latch members 48 proximate the area of their convergence. The latch members 48 also define a spacing 52 (in the general form of a "+") and have a triangular spacing 54 therebetween proximate their junction with the hollow interior of central portion 30. When a piercing element 12 is translated toward a retainer element 14 to interlock the elements 12, 14, the pin 20 enters the central portion 30, with the head 24 encountering the latch members 48 that converge downwardly into the pin receiver opening 50, thereby guiding the head 24 into the pin receiver opening 50. The latch members 48 are flexible and deform outwardly to accommodate the head 24 into the receiver opening 50. Once the latching head 24 has passed into the pin receiver opening 50, the latch members 48 return to their original unflexed configuration with the free ends thereof abutting the head 24 at the junction thereof with the shaft 22 of the pin 20 and preventing withdrawal of the pin 20 from its inserted position within the receiver member 14. In the event that a withdrawal force is exerted on the interlocked pin 20, the latch members 48 are drawn inwardly, reducing the diameter of the receiver opening 50 and the dimensions of the +-shaped spacing 52 and increasing the grip of latch members 48 on the shaft 22 of the pin 20, thus preventing withdrawal of the head 24 in the direction of disengagement. In the event that extreme disengagement force is applied, the shaft 22 will translate through one of the branches of the +-shaped space 52 and enter one of triangular spaces 54 and thereby lodge between two adjacent latch members 48 and the interior wall 56 of the central portion 30. This fall-back or failsafe position permits a greater degree of spacing between the inner surface 58 of the base 18 and the exterior surface 60 of the retainer element 14 (See FIG. 3) thereby releasing compressive force on the intervening tissue while retaining locking engagement of the elements 12, 14.

It should be appreciated that a greater or lesser number of latch members 48 could be employed within the scope of the present invention, e.g., a single latch member 48, a pair of opposed latch members 48 or multitude of latch members 48 could be utilized to capture the head 24. As a further alternative, the opening 32 may be completely or partially bridged by a penetratable diaphragm through which the head 24 penetrates and locks in the resulting aperture. FIG. 3 depicts optional redundant latch members 48' and a second latching head 24', either and/or both of which can be utilized to provide interlocking of piercing element 12 to receiver element 14 at two different depths of insertion of pin 20 into receiver element 14, e.g., to accommodate different tissue thicknesses. Additional redundant latching members 48' and/or heads 24' may be utilized to provide a greater engagement force, as well as a greater number of latching positions.

One or both of the abutting surfaces 58, 60 may be provided with grippers 61 that press into the surface of the anastomosed tissue or the gasket 16 to prevent rotation of the piercing element 12 and/or the receiver element 14, e.g., to prevent intrusion into the lumen of the anastomosed organ. It is preferred that the grippers 61 of the piercing element 12 be offset from those of the receiver element 14, to prevent the grippers 61 from piercing the anastomosed tissue.

The cross-sectional shape of the pin 20 may be circular or non-circular, e.g., hexagonal, octagonal, I-shaped, square, etc. In each case, the distal ends of the latch members 48 may be shaped such that the spacing 50 approximates the cross-sectional shape of the pin 20. If the pin 20 has a non-circular cross-sectional shape complementary to spacing 50, then these complementary elements 20, 50 tend to maintain their relative rotational orientation when the piercing element 12 is coupled to the receiver element 14, thus allowing the gripping elements 61 to be eliminated from one or the other element 12, 14, as applicable.

Figure 4:
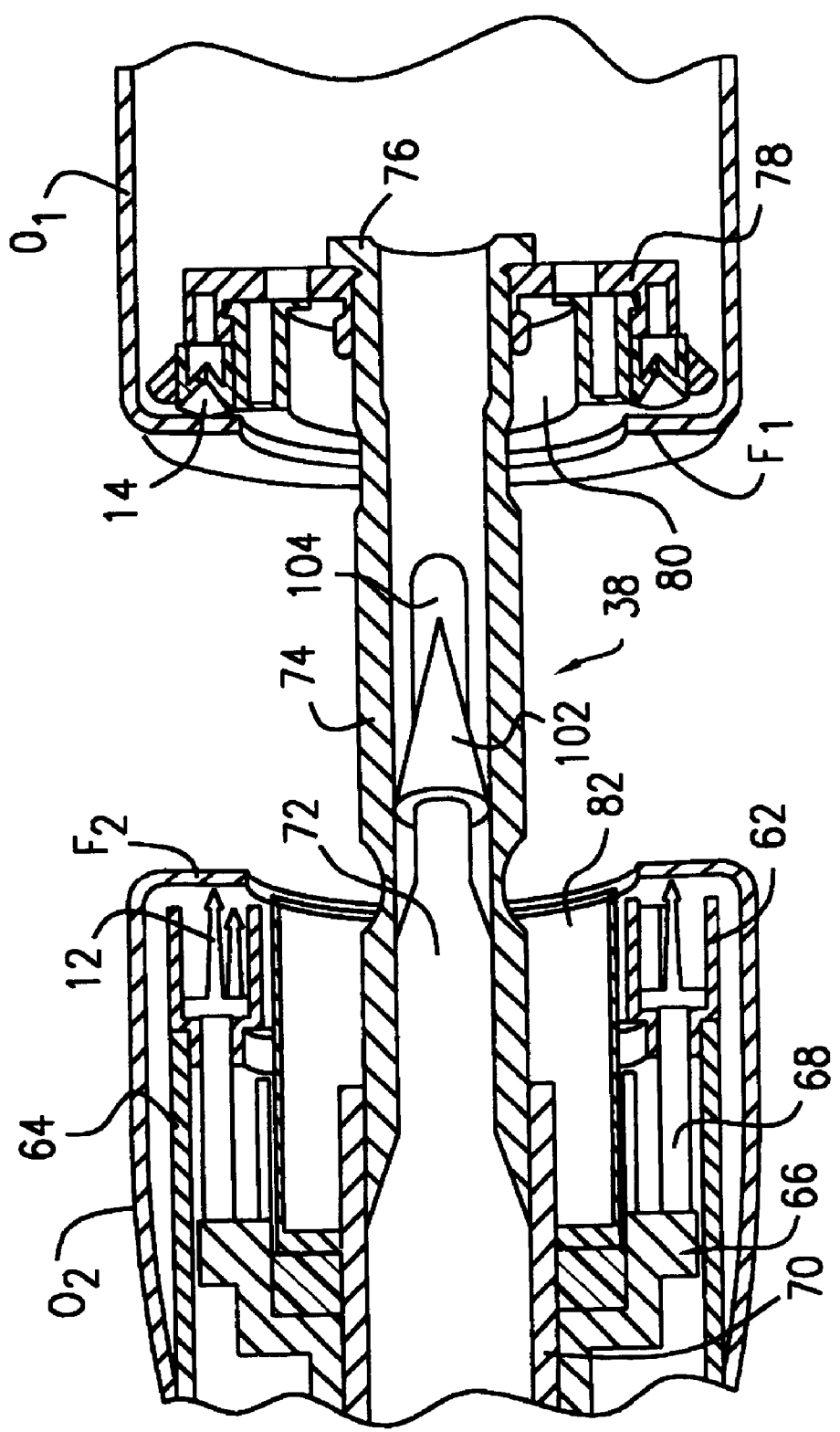
FIG. 4 is a cross-sectional view of the anastomotic fastener of FIGS. 1–3 in place within a dispenser for positioning the fastener within the disconnected sections of a tubular organ and closing the fastener to effect anastomosis.

FIG. 4 shows a dispenser 38 having a piercing element carrier 62 that holds one or more piercing elements 12, in a desired spatial configuration, e.g., in the circular arrangement shown in FIG. 1. If desired, a gasket 16 can be placed over the piercing elements 12 retained within the carrier 62, i.e., with the pins 20 extending through holes 46 in the gasket 16. In the alternative, the gasket 16 can be placed in front of the piercing elements 12 such that when the dispenser is actuated, the pins 20 of the piercing elements 12 penetrate the gasket 16. The carrier 62 is supported on a casing 64 and has at least one passage in the surface proximate the casing 64 that permits a moveable driver 66 to urge the piercing elements 12 in a forward direction, i.e., towards the retainer elements 14. The driver 66 may be provided with a plurality of drive pins 68 that extend through the carrier 62 to contact and displace corresponding piercing elements 12. The driver 66 is coaxially slideable over tube 70, which is typically formed from aluminum or stainless steel and provides a mechanical support and extension for positioning the carrier 62 within the organ to be anastomosed. An actuator pin 72 telescopes within the tube 70 and is removably coupled to a hollow actuator tube 74 in a manner which is known to those of normal skill in the art. More particularly, the dispenser 38 and actuator tube 74 are, except for features described specifically herein, substantially the same as commercially available, curved intraluminal stapler Model No. CDH25 available from Ethicon, Inc. of Cincinnati, Ohio. An exemplary dispenser 38 actuator mechanism and the coupling mechanism are also diagrammatically illustrated in FIGS. 5 and 6 described below.

The hollow actuator tube 74 has an outer diameter along at least a portion thereof which allows it to be telescoped into the tube 70 and has a flange 76 at one end for retaining a carrier 78 for the receiver elements 14. An annular cutting anvil 80 is coaxially positioned within the carrier 78. The cutting anvil 80 opposes a cylindrical knife 82 mounted on the driver 66. The dispenser 38 is shown with the carrier 78 extending into an open end of a first portion of a hollow organ $O_1$ and the carrier 62 and casing 64 extending into a second portion of the hollow organ $O_2$. In FIG. 4, the diameter of the carriers 62 and 78 are chosen to be slightly larger than the relaxed diameter of the organ portions $O_1$ and $O_2$. This relative sizing causes the organ portions $O_1$ and $O_2$ to form inwardly directed "flanges" $F_1$ and $F_2$. As is known in the art, the flanges $F_1$ and $F_2$, are typically established and maintained by "purse-string" sutures.

Having positioned the dispenser 38 as shown in FIG. 4, it may then be adjusted and actuated to cause the application of the fastener 10 to join the two divided organ portions O₁ and O₂. More particularly, the driver 66 of dispenser 38 has a specific "throw" or travel that is sufficient to project the piercing elements 12 out of the carrier 62, i.e., approximately the same distance as the distance from the base of the carrier 62 to the upper edge of the wall of the carrier 62.

Figure 5:
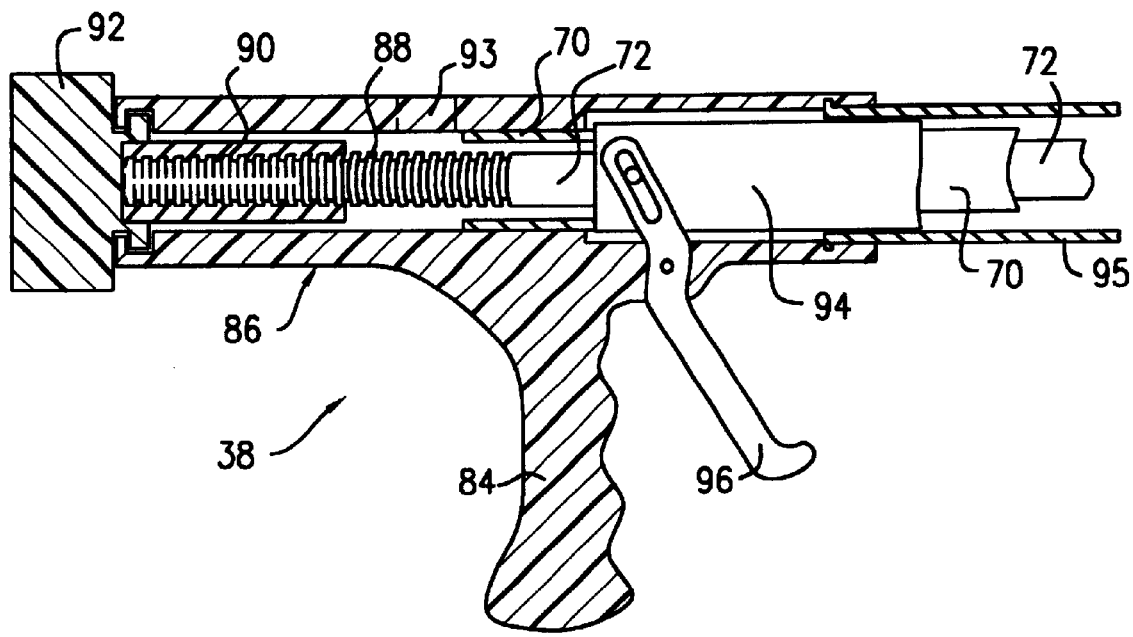
FIG. 5 is a diagrammatic cross-sectional view of an actuator mechanism for the dispenser shown in FIG. 4.
Figure 7:
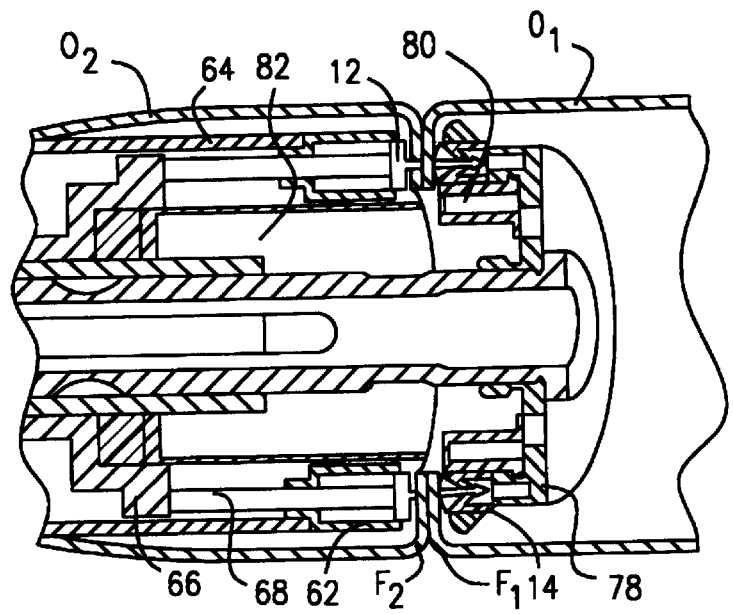
FIG. 7 is a cross-sectional view of the fastener and dispenser of FIG. 4 after anastomosis.

FIG. 5 illustrates a dispenser 38 having a handle 84 extending from a chassis 86. Tube 70 is attached at one end to the chassis 86. As noted above, the actuator rod 72 extends through the tube 70 and has a threaded end 88. The actuator rod 72 may include a flexible intermediate section, e.g., formed from cable, that permits the rod to be passed through a curved tube 70. An adjustment sleeve 90 threadedly engages end 88 to control the position of the actuator rod 72 relative to tube 70, i.e., by turning knob 92. A window 93 may be provided to visualize the position of the actuator rod 72. A driver tube 94 is coaxially slideable over tube 70 and is mechanically linked to driver 66 (see FIG. 4) to eject the piercing elements 12 from the carrier 62. Casing tube 95 shrouds the foregoing movable elements and serves as a mounting structure for casing 64. To apply the fastener array 10, the actuator pin 72 and hollow actuator tube 74 are drawn rearwardly by sleeve 90 acting upon threaded end 88. This action draws the two flanges F₁, F₂, together in apposition, as shown in FIG. 7. The trigger 96 is then pulled to drive the piercing elements 12 out of the carrier 62, through the two flanges F1, F2 of tissue and into locking engagement with the receiver elements 14 as shown in FIG. 3 and described above. The cylindrical knife 82 carried on the driver 66 is urged into contact with the anvil 80, simultaneously trimming excess tissue extending into the lumen formed at the junction of the two flanges F₁, F₂, when the driver 66 is actuated to dispense the piercing elements 12. The dispenser 38 can then be readjusted (via knob 92) such that the carrier 78 is displaced distally relative to the carrier 62, thereby allowing the carrier 78 to be disengaged from the receiver elements 14 that are now lockingly engaged to corresponding piercing elements 12 at the anastomosis. Unlike prior art anastomotic devices, the present invention utilizes a plurality of separate elements 12, 14, i.e., forming independent fasteners 11, which preserve the flexibility of the anastomosis, in particular, in the radial direction. As a result, the carrier 78 can be withdrawn through the anastomosis in its entirety and while remaining attached to the hollow actuator tube 74, namely, by pulling the carrier through the deformable anastomosis. The present invention therefore permits the material of the carrier 78 and cutting anvil 80 to be chosen based upon mechanical characteristics rather than being limited to an absorbable material. Since the dispenser 38 is removed in its entirety, leaving only the fastener 10 in the organ, there is less tendency for the organ to be obstructed or diminished in function other than that effect attributable to the anastomosis itself.

Figure 6:
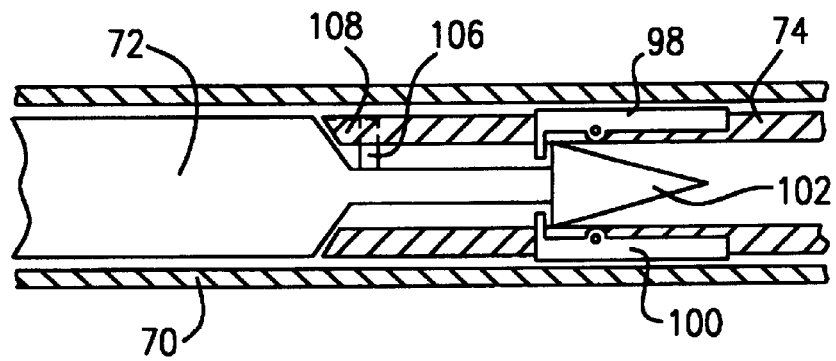
FIG. 6 is a diagrammatic cross-sectional view of a coupling mechanism for joining a removable actuator fitting to an actuator rod of the dispenser of FIG. 4.

FIG. 6 shows a releasable coupling mechanism whereby the actuator tube 74 engages the actuator pin 72. More particularly, the actuator tube 74 has one or more latch bars 98, 100 which pivot to admit the tapered tip 102 and then latch over the inner edge of the tip 102. The latch bars 98, 100 may be manipulated manually through corresponding access openings 104 provided in the actuator tube 74 (see FIG. 4), i.e., to open the latch bars 98, 100. The latch bars 98, 100 may be resiliently biased in the closed position. Commercially available Ethicon's intraluminal stapler Model No. CDH25 exhibits an exemplary latching mechanism which can be utilized in the dispenser 38 of the present invention to removeably couple the actuator tube 74 to the actuator rod 72. An alignment pin 106 mates to a corresponding slot 108 for establishing a predetermined orientation of the actuator tube 74, to the actuator pin 72. It is preferred that the dispenser 38 be provided with conventional mating registration features for establishing the relative orientation between the piercing elements 12 and the receiver elements 14, to insure that upon dispenser actuation, the pins 20 insert into the opening 50. Accordingly, the elements 12, 14 are registered in their respective carriers 62, 78 by mating complementary features, such as dowel pins/holes, facets, etc. The carriers 62, 78 are held at a selected orientation relative to the casing 64 and actuator tube 74, respectively, in a similar manner and the alignment pin 106 insures proper registration between the actuator rod 72 and actuator tube 74. It should be appreciated that the relatively large central opening 32 in central portion 30 of the receiver elements 14, as well as the inwardly sloping latch members 48 and pointed latching head 24, all contribute to guiding the pins 20 into the receiver openings 50 of the receiver elements 14. The configuration of the foregoing elements allows the elements 12, 14 to engage, even under conditions of non-optimal alignment and can compensate for misalignment caused by redirection of the pins 20 as they pass through the tissue to be anastomosed.

Figure 8:
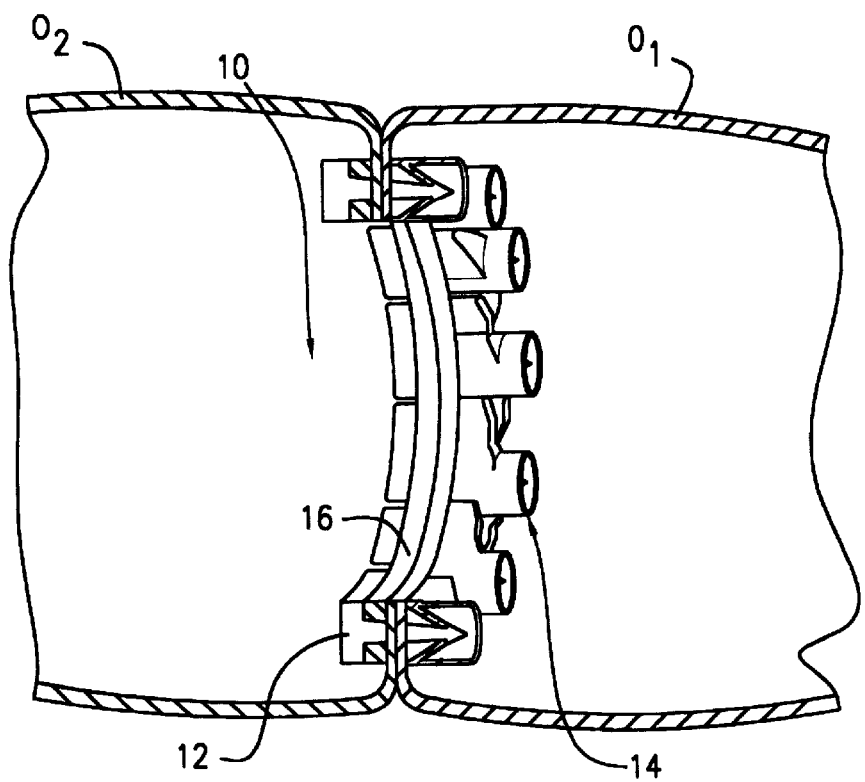
FIG. 8 is a cross-sectional view of the fastener of FIGS. 4 and 5 after the dispenser has been removed from the organ shown therein.

FIG. 8 shows the anastomotic fastener 10 in place holding the organ portions O₁ and O₂ in apposition. A gasket 16 is shown in FIG. 8 for the above-described purposes of distributing compressive force exerted by the fastener 10, bridging missing fastener elements 12, 14 and insuring apposition.

The elements 12, 14 may be formed from biocompatible polymers, such as aliphatic polyesters, polyorthoesters, polyanhydrides, polycarbonates, polyurethanes, polyamides and polyalkylene oxides. Alternatively, elements 12, 14 can be formed from biodegradable glasses or ceramics, such as calcium phosphates and other biocompatible metal oxides (i.e., CaO), metals or a combination of metals, biodegradable ceramics, glasses and polymers. The elements 12, 14 may also be formed from autograft, allograft, or xenograft bone tissues.

The gasket 16 is preferably composed of one of the following materials: fluoropolymers, polyurethanes, aliphatic polymers, poly(amino acids), copoly(etheresters), polyalkylenes oxalates, polyamides, poly(iminocarbonates), polyorthoesters, polyoxaesters, polyamidoesters, polyoxaesters containing amine groups, poly(anhydrides)and polyphosphazines.

In the preferred embodiment, at least one component of the circular anastomosis device is comprised of aliphatic polymer and copolymer polyesters and blends thereof. The aliphatic polyesters are typically synthesized in a ring opening polymerization. Suitable monomers include but are not limited to lactic acid, lactide (including L-, D-, meso and D,L mixtures), glycolic acid, glycolide, □-caprolactone, p-dioxanone (1,4-dioxan-2-one), trimethylene carbonate (1,3-dioxan-2-one), deltavalerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations thereof. These monomers generally are polymerized in the presence of an organometallic catalyst and an initiator at elevated temperatures. The organometallic catalyst is preferably tin based, e.g., stannous octoate, and is present in the monomer mixture at a molar ratio of monomer to catalyst ranging from about 10,000/1 to about 100,000/1. The initiator is typically an alkanol (including diols and polyols), a glycol, a hydroxyacid, or an amine, and is present in the monomer mixture at a molar ratio of monomer to initiator ranging from about 100/1 to about 5000/1. The polymerization typically is carried out at a temperature range from about 80° to about 240°, preferably from about 100° C. to about 220° C., until the desired molecular weight and viscosity are achieved.

In another embodiment of the present invention, the polymers and blends can be used as a therapeutic agent release matrix. To form this matrix, the polymer would be mixed with a therapeutic agent prior to forming the device. The variety of different therapeutic agents that can be used in conjunction with the polymers of the present invention is vast. In general, therapeutic agents which may be administered via the pharmaceutical compositions of the invention include, without limitation: antiinfectives such as antibiotics and antiviral agents; chemotherapeutic agents (i.e., anticancer agents); anti-rejection agents; analgesics and analgesic combinations; anti-inflammatory agents; hormones such as steroids; growth factors, including bone morphogenic proteins (i.e., BMPS's 1–7), bone morphogenic-like proteins (i.e., GFD-5, GFD-7 and GFD-8), epidermal growth factor (EGF), fibroblast growth factor (i.e., FGF 1–9), platelet derived growth factor (PDGF), insulin like growth factor (IGF-I and IGF-II), transforming growth factors (i.e., TGF-β I-III), vascular endothelial growth factor (VEGF); and other naturally derived or genetically engineered proteins, polysaccharides, glycoproteins, or lipoproteins. These growth factors are described in *The Cellular and Molecular Basis of Bone Formation and Repair* by Vicki Rosen and R. Scott Thies, published by R. G. Landes Company hereby incorporated herein by reference.

Matrix materials for the present invention may be formulated by mixing one or more therapeutic agents with the polymer. Alternatively, a therapeutic agent could be coated on to the polymer, preferably with a pharmaceutically acceptable carrier. Any pharmaceutical carrier can be used that does not dissolve the polymer. The therapeutic agent may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.001 percent to about 70 percent, more typically about 0.001 percent to about 50 percent, most typically about 0.001 percent to about 20 percent by weight of the matrix. The quantity and type of polymer incorporated into the drug delivery matrix will vary depending on the release profile desired and the amount of drug employed.

Upon contact with body fluids, the polymer undergoes gradual degradation (mainly through hydrolysis) with concomitant release of the dispersed drug for a sustained or extended period. This can result in prolonged delivery (over, say 1 to 5,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like. Following this or similar procedures, those skilled in the art will be able to prepare a variety of formulations.

The following examples describe exemplary materials and methods used in carrying out the present invention.

EXAMPLE 1

Piercing and receiving elements 12, 14 of the type discussed in this invention were fabricated out of biodegradable polymers via injection molding, attached, and tested for separation force.

The polymer used to form the piercing elements 12 was poly (glycolic acid), or PGA (Birmingham Polymer, Inc., Birmingham, Ala.). Poly (lactic acid), or PLA (Purac Biochem BV, Gorinchem, The Netherlands), was used to form the receiving elements 14. Both elements 12, 14 were formed using a commercial polymer injection molder (Nigata Type NN35M1, Nigata Engineering Co., Ltd., Japan). For the PGA piercing elements 12, the barrel temperature profile was 50, 235, 235, 230, 230° C. from the hopper to the injection port, with a mold temperature of 120° C. Maximum injection pressure was 83 $Kg_7/cm^2$. Injection and cooling times were 3 and 35 seconds, respectively. For the PLA receiving elements 14, the barrel temperature profile was 27, 210, 210, 205, 188° C. from the hopper to the injection port, with a mold temperature of 38° C. Maximum injection pressure was 127 $Kg_7/cm^2$. Injection and cooling times were 3 and 20 seconds, respectively.

Piercing elements 12 were inserted into receiving elements 14 by hand, and tested for separation force using an Instron Model 4501 universal testing machine. Special fixturing was used to maintain the applied force in the separation direction. Eight separation tests were conducted at a crosshead speed of 1 mm/min, and the tests were conducted at room temperature. The average pullout force measured was 4.62 pounds.

EXAMPLE 2

Piercing elements 12 and receiving elements 14 of the type described above were fabricated out of biodegradable polymers via injection molding. They were placed, along with a gasket 16, in a deployment system 38 for a circular anastomotic device, deployed in porcine colons, and the resulting anastomosis was tested for leak pressure.

The piercing elements 12 and receiving elements 14 used in the test were fabricated as discussed in Example 1. The gasket 16 material was a biodegradable polymer foam formed via the following lyophilization process.

Step A. Preparing 10% wt./wt. homogenous solution of 35/65 PCT/PGA in 1,4-Dioxane First, a 10% wt./wt. polymer solution of 35/65 poly (capralactone)/poly(glycolic acid) (35/65 PCL/PGA, Ethicon, Inc., Somerville, N.J.) in 1,4-Dioxane was prepared by dissolving 1 part 35/65 PCL/PGA with 9 parts of solvent 1,4-dioxane (Fisher Scientific, Fair Lawn, N.J.). The solution was prepared in a flask with a magnetic stir bar. To dissolve the copolymer completely, the mixture was gently heated to 70° C. and continuously stirred for 5 hours. A clear homogenous solution was then obtained by filtering the solution through a coarse porosity filter (Pyrex brand extraction thimble with fitted disc) using dry nitrogen to help in the filtration of this viscous solution.

Step B. Lyophilization

A laboratory scale lyophilizer (Model Freezemobile 6 of VIRTIS) was used. The lyophilizer used thermocouples attached to the shelves to monitor their temperature. At start-up, the shelf chamber was maintained at 20° C. for approximately 30 minutes. The homogenous polymer solution prepared in Step A was poured into a glass mold just before the start of the lyophilization cycle. The glass mold was optical glass 5.5 mm thick, and cylindrical with a 21 cm outer diameter and a 19.5 cm inner diameter. The lip height of the dish was 2.5 cm.

The mold with the solution was placed on the shelf of the lyophilizer, which was maintained at 20° C. The cycle was started and the shelf temperature was held at 20° C. for 30 minutes for thermal conditioning. Next, the solution was cooled to −5° C. by cooling the shelf to −5° C. After 60 minutes of freezing at −5° C., a vacuum was applied to initiate primary drying of the dioxane by sublimation. Primary drying under vacuum at −5° C. removed most of the solvent. At the end of this drying stage, the vacuum level reached was about 100 mTorr. Secondary drying under a 100 mTorr vacuum was done in two stages to remove the adsorbed dioxane. In the first stage, the shelf temperature was raised to 5° C. and held at that temperature for 1.5 hour. At the end of the first stage the second stage of drying was begun. In the second stage of drying, the shelf temperature was raised to 20° C. and held at that temperature for 1.5 hours. At the end of the second stage, the lyophilizer was brought to room temperature and the vacuum was broken.

The conditions described herein are typical and operating ranges depend on factors such as concentration of the solution, polymer molecular weights and compositions, volume of the solution, mold parameters, machine variables like cooling rate, and heating rates.

Leak pressure studies were conducted on porcine colons harvested from animals euthanized under IACUC approved studies. The colons were stored frozen until the day of the testing.

Piercing and receiving elements 12, 14, as well as a foam gasket 16 (2-mm thick) were loaded into a dispenser 38 as described earlier, and an anastomosis was performed connecting two pieces of the porcine colon.

The resulting anastomosis was tested for leak pressure as follows. One end of the anastomosed colon was clamped around a ½-inch tube. The other end was closed using a bowel clamp. The bowel clamp end was submerged in water so that the site of the anastomosis was approximately 1 cm below the surface. A catheter attached to a pressure transducer (Model EA6, Data Instruments, Wayland, Mass.) ran inside the tube to the site of the anastomosis. Air pressure was increased inside of the colon at a rate of 1 mm Hg/sec using an electronic pressure regulator (Model BB1-ME020, Proportion Air, McCordsville, Ind.). Leaks were detected at the site of the anastomosis when air bubbles rose from the site. In four tests, the average pressure achieved before air leakage was detected was 53.9 mm Hg.

It will be understood that the embodiments described herein are merely exemplary and that a person skilled in the art may make many variations and modifications without departing from the spirit and scope of the invention. All such variations and modifications are intended to be included within the scope of the invention as defined in the appended claims.

What is claimed is:

1. A surgical fastener, comprising:
    a plurality of first portions having a first tissue constraining surface;
    a plurality of second portions having a second tissue constraining surface, said first portions positionable proximate a first side of a bodily tissue, said second portions positionable proximate a second side of the bodily tissue adjacent corresponding ones of said first portions, said first portions extendable through the bodily tissue to contact said second portions and interlock therewith with said first tissue constraining surface positioned proximate the first side of the bodily tissue and resisting withdrawal of said first portions through the bodily tissue and said second tissue constraining surface positioned proximate the second side of the bodily tissue resisting withdrawal of said second portions through the bodily tissue, said first portions having a pin extending therefrom proximate said first tissue constraining surface and said second portions having a pin receiver opening therein proximate said second tissue constraining surface, said pin being lockingly received within said pin receiver opening, said first tissue constraining surface including a substantially flat base portion proximate said pin and first and second base extension arms extending from said base portion and having a width substantially less than a width of said base portion, said first and second base extension arms being spaced apart and extending generally tangentially from said base portion in opposite directions, said second tissue constraining surface including a central portion proximate said pin receiver opening and first and second central portion extension arms extending from said central portion substantially perpendicularly relative to an axis of said pin receiver opening, said first and second base extension arms and said first and second central portion extension arms being approximately coextensive and homologous.

2. The surgical fastener of claim 1, wherein said pin has a head at the free end thereof and said second portions have a hollow central portion with a cross-sectional area substantially larger than a cross-sectional area of said pin, said hollow central portion having an interior surface, and further including a plurality of latches extending from said interior surface proximate said second tissue constraining surface through said hollow central portion toward said receiver opening at a free end thereof, said head deforming said plurality of latches radially outward as said head enters said receiver opening, said head having a ledge at a junction of said head with said pin, said plurality of latches closing in upon said pin after said head passes said free ends of said plurality of latches with said free ends abutting said ledge when said pin is pulled in the direction of withdrawal of said pin from said receiver opening.

3. The surgical fastener of claim 2, wherein said free ends of said plurality of latches are separated by a spacing therebetween, said spacing being diminished when said pin is pulled in the direction of withdrawal causing said ledge to encounter said free ends and further converging said latches toward each other reducing the size of said retainer opening.

4. The surgical fastener of claim 3, wherein said plurality of latches are distributed around the internal periphery of said internal surface with a spacing therebetween proximate the junction of said plurality of latches with said internal surface, said junction spacing constituting a fall back receiver opening for retaining said pin by causing side surfaces of said plurality of latches to encounter and abut said ledge, capturing said head in said junction spacing.

5. The surgical fastener of claim 1, wherein said plurality of first portions are arranged in a predetermined spacial configuration adjacent to one another with a plurality of second portions arranged in homologous fashion with said first tissue constraining surfaces facing said second tissue constraining surfaces.

6. The surgical fastener of claim 5, further including a gasket interposed between said plurality of first portions and said plurality of second portions.

7. The surgical fastener of claim 6, wherein said gasket is divided into a plurality of segments by a plurality of radial slots.

8. The surgical fastener of claim 6, wherein said gasket is composed of a material selected from the group consisting of fluoropolymers, polyurethanes, aliphatic polymers, poly (amino acids), copoly(ether-esters), polyalkylenes oxalates, polyamides, poly(iminocarbonates), polyorthoesters, polyoxaesters, polyamidoesters, polyoxaesters containing amine groups, poly(anhydrides) and polyphosphazines.

9. The surgical fastener of claim 8, wherein said gasket is produced by lyophilization.

10. The surgical fastener of claim 8, wherein said gasket is biodegradeable.

11. The surgical fastener of claim 5, wherein said predetermined spacial configuration approximates a circle and said fastener is an anastomotic fastener.

12. The surgical fasteners of claim 11, wherein said fastener preserves radial flexibility of a resultant anastomosis to which it is applied.

13. The surgical fastener of claim 12, wherein said first portions and said second portions establish a compressive force on the anastomosed tissue in a configuration which approximates two concentric rings.

14. The surgical fastener of claim 1, wherein at least one of said plurality of first portions and said plurality of second portions is biodegradable.

15. The surgical fastener of claim 1, wherein said first portions are composed of a material selected from the group consisting of fluoropolymers, polyurethanes, aliphatic polyesters, poly(amino acids), copoly(ether-esters), poly-alkylenes oxalates, polyamides, poly(iminocarbonates), polyorthoesters, polyoxaesters, polyamidoesters, polyoxae-asters containing amine groups, poly(anhydrides), polypophazenes and bipolymers.

16. The surgical fastener of claim 1, wherein said first portions are composed of a biodegradeable material which acts as a therapeutic release matrix for release of at least one of the agents of the following group consisting of antibiotics, antiviral agents, chemetherapeutic agents, anti-rejection agents, analgesics, anti-inflammatory agents, hormones, steroids, growth factors, proteins, polysaccharides, glycoproteins and lipoproteins.

17. A surgical fastening system, comprising:
a fastener applicator having an elongated hollow tube with a handle at a first end;
an actuator rod extending through a lumen of said tube and extensible from a second end thereof;
a hollow actuator tube couplable at one end to said actuator rod and slideably insertable into said second end of said tube;
a first fastener carrier couplable to said actuator tube proximate a second end of said distal actuator fitting;
a casing tube disposed about said positioning tube proximate said second end of said positioning tube and having a free end which is substantially coaxial with said positioning tube and annularly spaced therefrom;
a second fastener carrier coupled to said free end of said casing tube;
a fastener driver disposed between said tube and said casing tube, said fastener driver having a retracted position and a dispensing position, said dispensing position being displaced a predetermined distance from said retracted position in a direction distal to said first end of said tube;
a trigger disposed proximate said handle for moving said fastener driver between said retracted position and said dispensing position;
a mechanical linkage extending between said trigger and said fastener driver;
an actuator rod adjuster for adjusting the spacing between said first fastener carrier relative to said second fastener carrier when said actuator rod is coupled to said actuator tube by adjusting the position of said actuator rod within said tube; and the surgical fastener of claim 1, wherein said plurality of first portions are insertable into said first carrier, said plurality of second portions are insertable into said second carrier, said first portions positionable proximate the first side of the bodily tissue when positioned within said first carrier, said second portions positionable proximate the second side of the bodily tissue adjacent corresponding ones of said first portions when positioned within said second carrier, said first portions extendable through the bodily tissue to contact said second portions and interlock therewith when said first portions are ejected from said first carrier by said fastener driver.

18. A surgical fastening system, comprising:
a plurality of individual fastener pairs each having a first portion with a first tissue constraining surface and a second portion with a second tissue constraining surface;
holding means for holding said plurality of individual fastener pairs in a generally circular array;
positioning means for positioning said first portions proximate a first side of a bodily tissue and said second portions proximate a second side of said bodily tissue adjacent corresponding ones of said first portions; and
ejecting means for ejecting said first portions from said holding means such that said first portions extend through the bodily tissue to contact said second portions and interlock therewith to form interlocking pairs.
said first tissue constraining surface of each of said first portions approximating a first pair of concentric circles, said second tissue constraining surface of each of said second portions approximating a second pair of concentric circles, the bodily tissue being clamped between said first pair of concentric circles and said second pair of concentric circles when said first portions and said second portions are interlocked.

19. The surgical fastener system of claim 18, further comprising cutting means for cutting excess tissue proximate said interlocking pairs.

20. A method for anastomosing tissue, comprising the steps of:
holding a plurality of individual fastener pairs each having a first portion with a first tissue constraining surface and a second portion with a second tissue constraining surface with said first portions proximate a first fraction of bodily tissue and said second portions proximate a second fraction of bodily tissue to be anastomosed to said first fraction of bodily tissue and adjacent corresponding ones of said first portions;
ejecting said first portions through the first and second fractions of bodily tissue; and
contacting said first portions with said second portions, said first portions and said second portions interlocking, each of first portions overlapping an adjacent one of said first portions and each of said second portions overlapping an adjacent one of said second portions, said first tissue constraining surface approximating a first set of concentric rings, said second tissue constraining surface approximating a second set of concentric rings.

21. The method of claim 20, wherein said steps of holding and ejecting are performed by a fastener dispenser and further including the steps of removing said second portions from said dispenser after said interlocking and passing said dispenser through said anastomosed junction by stretching said anastomosed junction radially outward.

* * * * *